United States Patent
Kubin

(10) Patent No.: US 8,980,772 B2
(45) Date of Patent: Mar. 17, 2015

(54) BARRIER FABRIC

(71) Applicant: Ceska Vcela s.r.o., Rakovnik (CZ)

(72) Inventor: Miroslav Kubin, Prague (CZ)

(73) Assignee: Ceska Vcela s.r.o., Rakovnik (CZ)

( * ) Notice: Subject to any disclaimer, the term of this patent is extended or adjusted under 35 U.S.C. 154(b) by 1 day.

(21) Appl. No.: 13/963,411

(22) Filed: Aug. 9, 2013

(65) Prior Publication Data

US 2014/0141216 A1    May 22, 2014

Related U.S. Application Data

(63) Continuation of application No. 13/174,818, filed on Jul. 1, 2011, now abandoned.

(30) Foreign Application Priority Data

Apr. 28, 2011  (CZ) ................................ PV 2011-249

(51) Int. Cl.
*B32B 27/02*    (2006.01)
*B32B 27/12*    (2006.01)
(Continued)

(52) U.S. Cl.
CPC .............. *A01N 25/34* (2013.01); *A47C 31/007* (2013.01); *B32B 5/022* (2013.01); *B32B 5/26* (2013.01);
(Continued)

(58) Field of Classification Search
CPC ...................................................... B82Y 40/00
USPC .............. 977/762; 5/500, 502, 699; 442/123, 442/381, 382, 400, 401, 415
See application file for complete search history.

(56) References Cited

U.S. PATENT DOCUMENTS

| 5,321,861 A | 6/1994 | Dancey et al. |
| 6,277,770 B1 | 8/2001 | Smith, III et al. |

(Continued)

FOREIGN PATENT DOCUMENTS

| CZ | 16987 U1 | 12/2006 |
| CZ | 297 697 B6 | 3/2007 |

(Continued)

OTHER PUBLICATIONS

Extended Search Report issued Oct. 20, 2011, in the corresponding European Patent Application No. 11005064.8-2313 (5 pages).

*Primary Examiner* — Matthew Matzek
(74) *Attorney, Agent, or Firm* — Buchanan Ingersoll & Rooney PC

(57) ABSTRACT

A barrier fabric with a nano-fibrous layer for mechanical retention of organic substances formed by a sandwich structure containing a basic material from unwoven fabric of "spunbond" type with areal weight of 15 to 50 g/m² to which at least one nano-fibrous layer is arranged, selected from hydrophilic polymer, a hydrophobic polymer, or in the case of double-layer arrangement, a combination of the hydrophilic polymer in one layer and the hydrophobic polymer in the other layer. The nano-fibrous layer is equipped with a protective covering layer, and the individual layers of the sandwich are connected to each other. The nano-fibrous layer has an organic polymer material with areal weight of 0.05 to 0.3 g/m² and thickness from 90 to 150 nm. The covering layer is selected from an unwoven fabric of "spunbond" type, "meltblown" type, cotton textile and/or a mixture of cotton and polyester.

7 Claims, 1 Drawing Sheet

Nano-fibrous layer PA6, diameter of fibres 145 nm

(51) Int. Cl.
*A01N 25/34* (2006.01)
*A47C 31/00* (2006.01)
*B32B 5/02* (2006.01)
*B32B 5/26* (2006.01)
*D04H 1/425* (2012.01)
*D04H 1/4382* (2012.01)

(52) U.S. Cl.
CPC ............ *D04H 1/425* (2013.01); *D04H 1/4382* (2013.01); *B32B 2262/0238* (2013.01); *B32B 2262/0292* (2013.01); *B32B 2307/7145* (2013.01); *B32B 2307/7265* (2013.01); *B32B 2307/728* (2013.01); *B32B 2307/73* (2013.01); *B32B 2307/764* (2013.01); *B32B 2535/00* (2013.01); *B32B 2571/00* (2013.01); *Y10S 977/762* (2013.01)
USPC ........... 442/123; 442/381; 442/382; 442/400; 442/401; 442/415; 5/500; 5/502; 977/762

(56) References Cited

U.S. PATENT DOCUMENTS

| | | |
|---|---|---|
| 2004/0026055 A1 | 2/2004 | Titus et al. |
| 2007/0175195 A1* | 8/2007 | Skirius et al. .................... 55/527 |
| 2008/0120783 A1* | 5/2008 | Knoff et al. ....................... 5/636 |
| 2011/0033673 A1* | 2/2011 | Kawka ........................... 428/196 |
| 2011/0041247 A1 | 2/2011 | Moon |

FOREIGN PATENT DOCUMENTS

| | | |
|---|---|---|
| DE | 42 31 010 A1 | 3/1994 |
| EP | 0 600 459 A1 | 6/1994 |
| EP | 1 190 652 A2 | 3/2002 |
| EP | 2 223 725 A1 | 9/2010 |
| JP | 2009-279930 A | 12/2009 |
| JP | 2010-274102 A | 12/2010 |
| WO | WO 2008/021293 A1 | 2/2008 |
| WO | WO 2010/074213 A1 | 7/2010 |

* cited by examiner

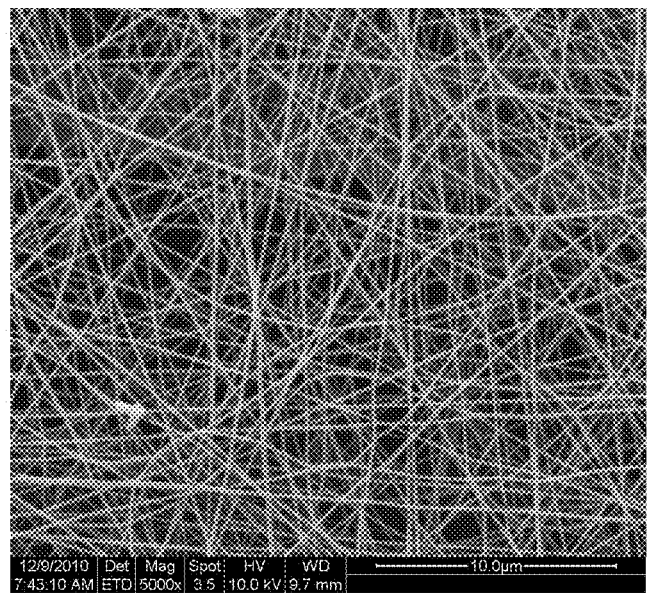
Fig. 1 Nano-fibrous layer PA6, diameter of fibres 145 nm
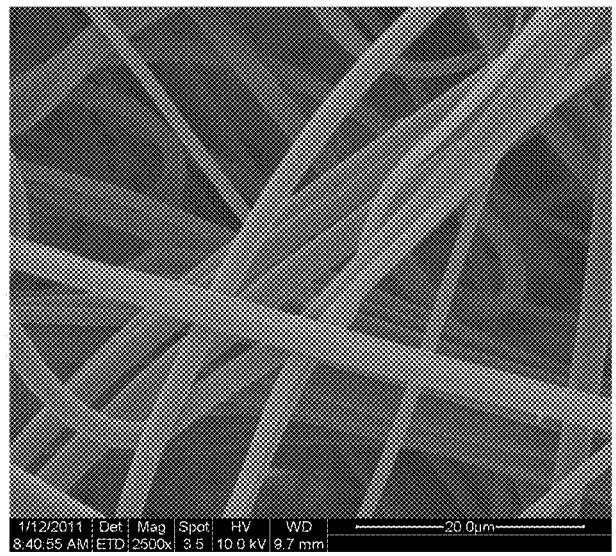
Fig. 2 "Meltblown" layer, diameter of fibres 1600 nm

BARRIER FABRIC

FIELD OF THE INVENTION

The invention refers to barrier textile fabrics containing at least one nano-fibrous layer which is used as a barrier preventing the penetration of microorganisms, allergens and dust particles, or also liquids, as the case may be.

DESCRIPTION OF THE PRIOR ART

The use of various textile materials as a barrier preventing the penetrating of bacteria, dust particles and allergens, or liquids, respectively, is common. These are mostly textiles or unwoven fabrics of "meltblown" or "spunbond" type.

The U.S. Pat. No. 6,277,770 and EP patent 1190652 describe the use of a micro-fibrous fabric which, thanks to its density, retains allergens in bedclothes and stops them from getting into the living space. The U.S. Pat. No. 5,321,861 describes a micro-porous material intended for the production of bedclothes, which is used as an upholstery cloth. The unwoven fabrics for production of bedclothes and furniture upholstery are also described in the document EP 0600459. The document DE 4231010 describes fabrics containing acaricides, which are intended for household cleaning.

Thanks to the ability to create a barrier, these materials may be used for health services, for domestic use or in hotel facilities. The existing materials that are currently used as barrier fabrics have various structures (predominantly textile fabrics and unwoven fabrics from micro-fibres), and various material composition (cotton, cotton mixtures in the case of textile fabrics; and polypropylene and polyester in the case of unwoven fabrics). The drawback of those materials is that either they are not able to ensure maximum possible protection, or they can provide the protection but with high material costs or with impairment of the comfort of the users. The textiles used as allergen barriers in bedclothes can be mentioned as an example. Woven materials can retain approximately 95% of allergens; however, their manufacture is exacting, as regards the materials and technology, which affects the resulting price of the material or the final products. Barrier materials preventing liquid penetration are another example. The only type of bed protection that is able to retain liquids is bed upholstery made of artificial leather or plastic materials. Such upholstery, however, is air-tight, and therefore it cannot provide sufficient comfort for the user, for example in a situation when a patient is dependent on round-the-clock confinement to bed. The air-tightness, in combination with poor positioning, may cause grazes and bed sores on the patient's body.

The use of nano-fibrous layer for the barrier fabrics is described, e.g. also in the document 2004026055, where the textile fabric is intended for the production of surgical gowns and surgical coverings. This is produced from unwoven fabric and is covered by nano-fibres to enhance the barrier properties of the material; the nano-fibrous layer is made of thermoplastic polymers. The use of thermoplastic polymer is advantageous because it provides adhesion between the nano-fibrous layer and the base material.

SUMMARY OF THE INVENTION

The subject of this invention is a barrier fabric with a nano-fibrous layer for mechanical retention of organic substances. The essence of the invention is that the barrier fabric is created by a sandwich containing a basic material made from unwoven fabric of "spunbond" type with areal weight of 15 to 50 $g/m^2$ to which at least one nano-fibrous layer is arranged, selected from the group involving a hydrophilic polymer, a hydrophobic polymer, or in the case of double-layer arrangement, a combination of the hydrophilic polymer in one layer and the hydrophobic polymer in the other layer, and where the nano-fibrous layer is equipped with a protective covering layer, and the individual layers of the sandwich are connected to each other, and where the nano-fibrous layer used as the barrier against penetration of allergens produced by the dust mites through the upholstery material of a mattresses, pillows, bed-clothes or soft furnishings, is created by an organic polymer material with areal weight of 0.05 to 0.3 $g/m^2$ and thickness from 90 to 150 nm, whereas the covering layer is selected from the group involving an unwoven fabric of "spunbond" type, "meltblown" type, cotton textile and/or a mixture of cotton and polyester. Advantageously, the areal weight of the nano-fibrous layer can range from 0.1 to 0.15 $g/m^2$ and the thickness can be in the range of 100 nm.

The base material, advantageously, is an unwoven fabric of "spunbond" type; the nano-fibrous layer may be made from the hydrophilic polymer PA6 of the polyamide group. The nano-fibrous layer may include the additive of acaricides as well.

In comparison with the current state, especially the increased effectiveness of mechanical capture of organic substances, and lower purchase costs of the barrier fabric are beneficial.

The reason for applying two nano-fibrous layers in the sandwich structure of the barrier fabric may be the different physical characteristics of the polymers used (hydrophobic feature or the hydrophilic feature, respectively), or the attainment of different porosity at the individual layers made from the same polymer materials; the content of biologically active additive is applied to one side of the nano-fibrous layer only.

Another variation of the invention is a sandwich type barrier fabric with a nano-fibrous layer for the mechanical capturing of organic substances; the sandwich structure contains a basic material made from unwoven fabric of "spunbond" type with areal weight of 15-50 $g/m^2$, at which is arranged and to which is attached at least one nano-fibrous layer, thus creating a barrier that prevents penetration of microorganisms, including bacteria and viruses; this can be used as material for surgery gowns, mouth-screens, coverings or biological filters, where the nano-fibrous layer is created by an organic hydrophobic polymer material made from polyurethane or PVDF fluoro-polymer, or by their co-polymers, respectively, with areal weight of 0.05 to 0.2 $g/m^2$ and thickness ranging from 100 to 250 nm. Advantageously, the areal weight of nano-fibrous layer can range from 0.1 to 0.15 $g/m^2$ and the thickness in the range of 170 nm. The nano-fibrous layer may include an additive of antimicrobial substance.

Further variation of the invention is a sandwich type barrier fabric with a nano-fibrous layer intended for capturing of physiological liquids, e.g. water, blood or urine; the sandwich structure contains a basic material made from unwoven fabric of "spunbond" type with areal weight of 15 to 50 $g/m^2$, at which is arranged and to which is attached at least one nano-fibrous layer made from a hydrophobic polymer material from polyurethane or from PVDF fluoro-polymer, or from their co-polymers, respectively, with areal weight of 2 to 10 $g/m^2$ and thickness from 100 to 250 nm. Thickness of the nano-fibrous layer is advantageously in the region of 150 nm.

The advantage of use of the nano-fibrous layer or layers according to this invention is namely the lower demand for materials; the barrier is formed by a nano-fibrous layer or layers with very low overall areal weight. Nevertheless, the layer allows retention of 99.9% of microorganisms and allergens, and is capable of capturing liquids as well.

BRIEF DESCRIPTION OF DRAWINGS

FIG. 1 shows unwoven fabric using "spunbond" technology; and

FIG. 2 shows unwoven fabric produced by "meltdown" technology.

EXAMPLES OF PREFERRED EMBODIMENTS

The barrier fabric according to this invention is based on the use of the nano-fibrous layer. Thanks to its structure, this layer provides sufficient barrier properties, based on the mechanical retention of microorganisms (bacteria and viruses), allergens produced by the dust mites (their excrements), and also the molecules of physiological liquids (water, urine, blood) even in very thin layers. The capability of such mechanical capture depends on the size of pores in the nano-fibrous layer, and on the surface wettability of the nano-fibrous layer. The size of the pores depends on the diameter of nano-fibres in the layer, and on the layer thickness. The surface wettability relates to the selection of material (polymer) and to the surface tension of the polymer nano-fibrous layer.

To provide mechanical cohesion of the nano-fibrous layer material, the subsequent workability of barrier fabrics into the final product, and not least, also the lifetime of products that are made of them, the barrier fabric according to this invention has the form of a three- to four-layer sandwich where both outside layers (the nano-fibrous layer carrier and the covering layer) are made of classical textile materials (woven fabric, unwoven textile of "spunbond" type, unwoven textile of "meltblown" type, combination of unwoven materials of "spunbond/melt blown" type), and the inside layer or both inside layers are from the nano-fibrous material.

The advantage of use of the nano-fibrous layer or layers is a lower demand for materials; the barrier is created by the nano-fibrous layer or layers with total areal weight of 0.05 to 3.0 $g/m^2$. Nevertheless, the layer allows the retention of 99.9% of microorganisms and allergens, and is able to capture liquids as well.

The material used for the internal layers is selected for the individual applications with respect to the required manufacture qualities of the initial sandwich, and regarding the total purchase costs of the resulting material. The most cost-effective variant of the sandwich composition is the combination of unwoven fabric of "spunbond" type (the carrier of nano-fibrous layer)—nano-fibrous layer—unwoven fabric of "spunbond" type (covering layer), which may be used for surgical cloths and surgical coverings in health services, but also for upholstery and mattresses resistant to water penetration and allowing the capture of allergens, whereas both of those features may be combined advantageously in one product. Nevertheless, a sandwich involving a woven textile at one external side (outside covering layer of upholstery), and unwoven fabric of "spunbond" type at the other external side (inside of upholstery, creating a carrier of the nano-fibrous layer) may be used for the upholstery for mattresses and bedclothes. This combination can provide the same barrier characteristics (capture of allergens, resistance to penetration of liquids), but the resulting product will have the feel parameters of a classical textile material used for domestic purposes, and not the characteristics typical for a technical textile, such as the "spunbond" or "meltblown" types by themselves.

As regards the purpose of use, the fabrics may be produced from cotton or a mixture of cotton and polyester, or from polyacrylonitrile and its mixtures respectively, etc., by classical weaving technologies. The textile structure may be either plain weave, sateen or jacquard weave; the resulting areal weight of fabric may vary from 30 $g/m^2$ up to 200 $g/m^2$. Higher areal weights are also acceptable; however the material need would be over-designed and therefore not economical.

The essence of the production of unwoven fabric using the "spunbond" technology (FIG. 1) is in direct spinning of polymeric granulate into endless fibres (filaments) and the subsequent creation of a flat unwoven fabric. By this method, the characteristic primary production of fibres and their subsequent conversion into an areal formation may be simplified into one production step. The source used for the production of this type of unwoven fabric is polypropylene—mono-fibres, or a combination of polypropylene and polyurethane—bi-component fibres. The range of areal weight of the unwoven materials is 10 to 100 $g/m^2$.

The unwoven fabrics produced by the "meltblown" technology (FIG. 2) are manufactured by extrusion of a polymer melt through nozzles, where very fine fibres are created from the polymer melt by the effect of flowing air. The source used for the production of this type of unwoven fabric is polypropylene or polyester.

According to this invention, the barrier fabric containing nano-fibres, intended for use in health services, forms a barrier preventing penetration of microorganisms from the external environment into a wound during surgical intervention in medical facilities. They have the ability to capture 99.9% of microorganisms from the air, while simultaneously maintaining good air permeability of the material, with low material consumption. These textile materials are intended for clothes for surgical staff and for surgical coverings. These materials may be further used for field hospitals as the textile separating the surgical area from the surrounding environment. The contamination of the surgical wound by bacteria from the outside environment (generally as a hospital infection) represents a frequent post-operative complication during the convalescence of patients after a surgical intervention.

According to this invention, the barrier fabric containing nano-fibres, intended as a barrier preventing penetration of allergens produced by dust mites, may be applied in domestic use or in hotel facilities. They may also be used for production of safety covers for mattresses, pillows, blankets, and upholstery for armchairs and chairs, in which the allergens produced by dust mites are commonly present, and it is practically not possible to remove them. A safety cover with the nano-fibrous layer creates an enclosure for the material containing allergens, and keeps them inside. At the same time, it does not allow the penetration of mite food sources (skin flakes, organic particles) and humidity inside the mattress, blanket or upholstery. The mites stop propagating and die if they lose the environment and conditions suitable for their survival.

Furthermore, the barrier fabrics according to this invention, containing nano-fibres, may be used as a barrier against the penetration of liquids, e.g. as a protective cover for a mattress preventing liquid penetration (physiological liquids—blood, urine, water) in hospitals and for home nursing of adults and children, and for protection against liquid penetration (water, coffee, drinks) in hotel facilities. When a mattress or blanket is enclosed in a protective cover made from the barrier fabric, the liquids cannot infuse in the product, and it cannot be damaged; the liquids will run down along the protective cover.

The essence of the invention lies in the use of a very thin nano-fibrous layer (0.03 to 1.0 g/m$^2$) as a barrier layer for the capture of bacteria, viruses and allergens that are produced by dust mites. The capture of microorganisms and allergens is assured on the principle of mechanical filtration, and this effect may be further enhanced by addition of a bio-active substance in the nano-fibrous structure. This substance will actively kill the captured microorganisms (the material will have germicide effects) or the dust mites producing allergens, respectively.

With respect to the very thin thickness of the nano-fibrous layer (0.1 to 100 μm) and the layer areal weight (0.1 to 5 g/m$^2$) and to the insufficient mechanical strength of this layer resulting from those facts, the nano-fibrous layer has to be imbedded on a carrier layer, and advantageously complemented with an additional covering layer. Therefore the barrier fabric containing nano-fibres has a sandwich form.

The size of pores in the sandwich with the barrier fabric with average thickness of fibres of approximately 100 to 150 nm is 0.1 μm to 5 μm in one layer, but predominantly the size of pores is below 1 μm.

Bacteria size varies in units of micrometers: 2-5 μm (*E. coli* 5 μm). The size of viruses is within the range of 50 to 800 nm (influenza RNA virus Orthomixoviridae 80 nm). The size of allergens that are produced by dust mites varies within the range of 10 to 40 μm.

Therefore a barrier material with content of nano-fibrous layer (produced advantageously from hydrophobic polymer) with fibre diameter from 150 to 500 nm, porosity approximately 200 nm to 5 μm and areal weight of approximately 0.05 to 0.2 g/m$^2$ will be sufficient for the capture of bacteria. When the fibres in the layer will have diameters smaller than 100 nm, the areal weight of the layer acting as the required retaining material may be lower—0.03 to 0.1 g/m$^2$. This barrier material may be used for production of surgical clothes, mouth-screens, gowns and surgical coverings for clean areas.

For the capture of viruses, it is necessary to use barrier material with content of nano-fibrous layer (produced advantageously from hydrophobic polymer) with fibre diameters of 50 to 150 nm, porosity approx. 50 nm to 1 μm and areal weight approx. 0.05 to 0.2 g/m$^2$. This barrier material may be used for production of mouth-screens for protection of the respiratory system, and again for the surgical clothes, mouth-screens, gowns and surgical coverings for clean areas.

The barrier material with content of nano-fibrous layer (produced advantageously from hydrophilic polymer PA6 from the polyamide group) with fibre diameters from 100 to 500 nm, and porosity 200 nm to 5 μm and areal weight 0.03 to 0.1 g/m$^2$ is sufficient for capture of allergens. When the fibres in the layer will have diameters smaller than 100 nm, the areal weight of the layer acting as the required retaining material may be lower—0.03 to 0.1 g/m$^2$. This material can be used for the manufacture of upholstery for mattresses, blankets and pillows, covering upholstery for chairs, armchairs, etc.

For the manufacture of barrier material with content of nano-fibres, it is possible to use advantageously a hydrophobic polymer from polyurethane or PVDF fluoro-polymer, or from their co-polymers, respectively, where the nano-fibrous layer with fibre diameter from 150 to 500 nm and areal weight from 2 to 10 g/m$^2$ creates a sufficient barrier against water penetration.

The mechanical retention of microorganisms and allergens may be enhanced by addition of a bio-active substance in the nano-fibrous structure that will actively exterminate the captured microorganisms. In the case of viruses and bacteria, a part of the nano-fibrous material may be an antimicrobial substance (silver, chlorhexidine, quaternary salts, etc.). In the case of barrier materials that are able to capture allergens, a part of the nano-fibrous layer may be acaricide, which exterminates mites on contact, i.e. the originators of allergens (phenylmethyl benzoate, sulphide). To achieve a biological effect, it is suitable to add an antimicrobial substance into the spinning solution in the quantity of 100 ppm up to 5% of the substance in the polymer dry matter.

The nano-fibrous layers are prepared from solutions of organic polymers (PA6, PAN, PUR, PVDF, etc.) by the method of electro-spinning without use of needles.

For the manufacture of barrier fabrics intended as materials for surgical gowns and mouth-screens, it is advisable to use hydrophobic polymers (e.g. PVDF, PUR, etc.). It is advisable to use the hydrophobic polymer also for materials intended for barriers against liquid penetration. It is possible to achieve resistance against water penetration of 3000 mm or more, measured by the water column method. For the materials intended as a barrier against penetration of allergens from bedclothes and mattresses, it is possible to use the nano-fibres from the polymers PA6, PAN, PET, etc.

With respect to the very small thickness of the nano-fibrous layer (0.1 to 10 μm) and to the insufficient mechanical properties of this layer resulting from this fact, the nano-fibrous layer has to be imbedded on a carrier layer (substrate), and advantageously complemented with an additional covering layer. The carrier layer is fundamental also due to the manufacturing principle itself, where the nano-fibrous layer is deposited over a carrier layer (substrate) during the spinning from a polymer solution The nano-fibrous layer is covered by the covering layer for the reason of protection and retention of its homogenity, and therefore maintaining the barrier properties of the nano-fibrous layer during subsequent processing into a final product (cutting, sewing, welding), and during the usage of the resulting product.

The resulting product has the form of a sandwich that contains: substrate/nano-fibrous layer/covering layer of substrate, respectively/nano-fibrous layer/nano-fibrous layer/covering layer. The reason for the producing of two nano-fibrous layers in the sandwich structure of the barrier fabric may be the different physical characteristics of the polymers used (hydrophobic feature or the hydrophilic feature, respectively), or the attainment of different porosity at the individual layers made from the same polymer materials; the content of biologically active additive is applied to one side of the nano-fibrous layer only.

When it is necessary to provide good adhesion of the nano-fibrous layer to the substrate during its manufacture, it is possible to use an adhesive solution which is deposited homogenously to the substrate to which the nano-fibres are imbedded. Cohesion of the protective layer with the nano-fibrous layer and substrate is assured by a lamination principle. Lamination may be achieved by the use of adhesives (powders, pastes), or the lamination may be achieved merely by application of heat and pressure.

The substrate (carrier material) is wound on a roll and passes through a chamber in which the nano-fibres are produced by electrostatic spinning method. The covering material is unreeled from a roll and is subsequently powdered by a defined quantity of adhesives. Connection between the fibrous substrate and covering layer is done in a lamination machine with use of high temperature and pressure, respectively. The resulting sandwich is wound on a roll. The process for manufacture of the sandwich may be continual (the process described above), or discontinuous. In the case of a discontinuous process, the substrate is first fibrillated with the nano-fibrous layer and wound on a roll. The substrate is subsequently unreeled from this roll and connected with the covering layer in the lamination process.

The carrier material (substrate) is a textile onto which the barrier nano-fibrous layer is deposited. As the substrate, it is possible to use various types of textiles. Selection of a suitable textile relates to the anticipated usage parameters of the product and the acquisition price of the material. For the single-use products (surgical gowns, mouth-screens, protective mattress covers against liquids), it is suitable for both technical and economical reasons to apply the unwoven textiles of "spunbond", "spunbond/meltblown" or "bi-component spunbond" type. These textiles have the required mechanical properties (strength), air permeability and dimensional tensile stability, so that the nano-fibrous layer, and therefore the barrier abilities of the material, could not be damaged either during processing or the final use of the product. An undisputable advantage of the use of unwoven fabrics is their low production cost. "Spunbonds" are produced in areal weights 10 to 100 g/m$^2$. The materials with areal weight of 18 to 35 g/m$^2$ seem to be a suitable substrate; for the covering layer, the materials with 10 to 20 g/m$^2$ are sufficient.

The substrate and the covering layer may also be fabrics with sufficient dimensional stability (areal weight 35 to 150 g/m$^2$); nevertheless, their production costs are several-fold higher. Compared to unwoven fabrics, they have a better feel, and represent a material which is used traditionally in the area of soft furnishings.

As was mentioned already above, the nano-fibrous layer is produced from a polymer solution or melt (PA, PUR, PAN, PET, PP, etc.), using the process of electrostatic spinning, based on a technology without the use of needles, and the layer is deposited over a carrier material (substrate) during the process of its production. Selection of a polymer suitable for the production of the nano-fibrous layer for barrier fabrics is influenced by the possibility to achieve the required porosity of the layer, with respect to the size of captured microorganisms and allergens. The layer thickness (areal weight) is governed by the requirements for the barrier properties of the respective material. This layer may involve biologically active additives—antimicrobial substances, in the case of use as a barrier textile for the manufacture of medical gowns, mouth-screens, surgical coverings—acaricides, in the case of the manufacture of barrier textiles preventing the penetration of allergens.

The covering layers may be again of various types of unwoven fabrics or textiles, respectively. Selection of a textile relates to the required usage parameters of the final product, with respect to a competitive price of the product on the market.

a) Application of barrier textiles in the products as surgical clothes in clean areas, used as means in health services (surgical mouth-screen, gown)—barriers against penetration of microorganisms (bacteria, viruses).

Example 1

Sandwich: unwoven fabric of "spunbond" type—nano-fibrous layer—unwoven fabric of "spunbond" type. "Sunbond" areal weight (substrate and covering layer) 10 to 50 g/m$^2$, nano-fibrous layer from hydrophobic polymer (PVDF, PUR, PP, etc.) areal weight of the nano-fibrous layer 0.05 to 0.2 g/m$^2$, fibre diameters 150 to 170 nm, adhesion between the individual layers is provided by adhesives or by lamination, or by combination of both methods, respectively. An optimum combination as regards the usage characteristics and the production costs: "spunbond" substrate 20 g/m$^2$, nano-fibrous layer PVDF 0.1 g/m$^2$ with thickness 170 nm, "spunbond" covering layer 15 g/m$^2$).

Also another unwoven type of textile may be used as the substrate or the covering layer, e.g. "meltblown" or "spunbond/meltblown". The nano-fibrous layer may contain antimicrobial substances (silver in nano-crystallic or micro-crystallic form, chlorhexidine, quaternary salts, etc.).

Example 2

Sandwich composition: unwoven fabric of "spunbond" type—1st nano-fibrous layer—2nd nano-fibrous layer—unwoven fabric of "spunbond" type, "spunbond" areal weight (substrate and the covering layer) 10 to 50 g/m$^2$, 1st nano-fibrous layer from hydrophobic polymer (PVDF, PUR, etc.) areal weight 0.02 to 0.1 g/m$^2$ and fibre diameters 150 to 170 nm, 2nd nano-fibrous layer from hydrophilic polymer (PA, PVA, etc.) areal weight 0.02 to 0.1 g/m$^2$ and fibre diameters 50 to 250 nm. Adhesion between the individual layers is provided by depositing of adhesives to the substrate before imbedding the fibrous material, or by lamination of the sandwich, or by combination of both methods, respectively. An optimum combination as regards the usage characteristics and the production costs: "spunbond" substrate 20 g/m$^2$, 1st nano-fibrous layer PVDF 0.1 g/m$^2$, 2nd nano-fibrous layer PA6 0.05 g/m$^2$, covering layer "spunbond" SB 15 g/m$^2$.

The 1st and 2nd nano-fibrous layers differ from each other by the used polymer (e.g. hydrophobic PVDF or PUR and hydrophilic PA6), or by porosity in the case of using the same polymers, e.g. PA6 with fibre diameters 100 nm (porosity 0.1 to 2 μm) and PA6 with fibre diameters 200 nm (porosity 0.5 to 5 μm).

Alternatively, the 1st or 2nd nano-fibrous layer contains antimicrobial substances (silver in nano-crystallic or micro-crystallic form, chlorhexidine, quaternary salts, etc.).

b) Application of barrier fabrics in upholstery products and in covering materials for bedclothes, mattresses, furniture padding, soft furnishings—barrier against penetration of allergens and mites.

Example 3

Sandwich: unwoven fabric of "spunbond" type—nano-fibrous layer—unwoven fabric of "spunbond" type. The "spunbond" areal weight (substrate with covering layer) 15 to 50 g/m$^2$, nano-fibrous layer from a hydrophilic or hydrophobic polymer (PA, PAN, PVDF, PET, PP, etc.) areal weight 0.05 to 0.3 g/m$^2$, fibre diameters 100 to 500 nm, ideally 100 nm. Adhesion between the individual layers is provided by depositing of adhesives to the substrate before imbedding the fibrous material, or by lamination of the sandwich, or by combination of both methods, respectively. An optimum combination as regards the usage characteristics and the production costs: "spunbond" substrate 20 g/m$^2$, nano-fibrous layer PA6 0.1 g/m$^2$, "spunbond" covering layer/layers 20 g/m$^2$).

The nano-fibrous layer may contain acaricides (phenylmethyl benzoate, sulphide).

The substrate or the protective layer, or both layers are textiles, areal weight 50 to 150 g/m$^2$, adhesion between the individual layers is provided by deposition of adhesives to the substrate before imbedding the fibrous material, or by lamination of the sandwich, or by combination of both methods, respectively. An optimum combination as regards the usage characteristics and the production costs: "spunbond" substrate 20 g/m$^2$, nano-fibrous layer PA6 0.1 g/m$^2$, covering layer from a fine textile with plain weave (approx. 45 warp threads and 30 quill threads in 1 cm², yarn tenuity 10-15 Tex).

c) Application of barrier fabrics in products as protective covers for mattresses against liquids (prevention of penetration of physiological liquids: blood, urine), drinks (coffee, tea, sweetened and ionic drinks) and water.

Example 4

Sandwich: unwoven fabric of "spunbond" type—nano-fibrous layer—unwoven fabric of "spunbond" type. "Spunbond" areal weight (substrate and covering layer) 15 to 50 g/m², nano-fibrous layer from hydrophobic polymer (PVDF, PUR, PP, etc.) areal weight 1-10 g/m², fibre diameters 100 to 500 nm; adhesion between the individual layers is provided by deposition of adhesives to the substrate before imbedding the fibrous material, or by lamination of the sandwich, or by combination of both methods, respectively. An optimum combination as regards the usage characteristics and the production costs: "spunbond" substrate 20 g/m², nano-fibrous layer PVDF 4 g/m² with thickness 150 nm, "spunbond" covering layer 20 g/m²).

Alternatively, the substrate or the protective layer or both layers are textiles, areal weight 50 to 250 g/m², adhesion between the individual layers is provided by adhesives, or by lamination of the sandwich, or by combination of both methods, respectively. An optimum combination as regards the usage characteristics and the production costs: "spunbond" substrate 20 g/m², nano-fibrous layer PVDF 4 g/m², covering layer from a fine textile with plain weave (approx. 45 warp threads and 30 quill threads per 1 cm², yarn tenuity 10 to 15 Tex).

INDUSTRIAL USE

The invention is applicable in products used as a barrier against penetration of microorganisms (bacteria, viruses), in surgical clothes intended for clean areas, used as means in health services (surgical mouth-screen, gown, surgical coverings). The barrier fabric may be used for the production of a whole product, or for a part of a product, respectively (front side of a surgical gown, strengthening in the area around the surgical wound, etc. This fabric may be further used in products that should have the barrier function against penetration of allergens and mites, as covers for bedclothes (pillow, blanket), covers for mattresses (the mattress is enclosed by the cover either completely or partially). They may form a part of furniture padding and external covers of chairs, armchairs, mattresses, etc. They may also be used as an individual layer under the upper layer of a furniture padding or upholstery, or may form a part of other house textiles like drapes and curtains. For barrier textiles that are intended as a barrier against the penetration of allergens and mites, their barrier properties may also be used advantageously against penetration of liquids, provided that the nano-fibrous layer has been manufactured from a hydrophobic polymer. Those textiles may be used either for upholstery of a mattress or as a part of furniture padding and facing.

Barrier fabrics that are intended as barriers preventing penetration of liquids may be used for the upholstery for mattresses, beds, armchairs and chairs (their textile part is completely or partially enclosed in the upholstery).

The invention claimed is:

1. A barrier fabric with a nano-fibrous layer for mechanical retention of organic substances, which is formed by a sandwich structure containing a basic material from unwoven spunbound fabric with areal weight of 15 to 50 g/m² to which at least one nano-fibrous layer is arranged, selected from the group comprising a hydrophilic polymer, a hydrophobic polymer, or a combination of a hydrophilic polymer in one layer and a hydrophobic polymer in another layer to form a double layer arrangement, and where the nano-fibrous layer is equipped with a protective covering layer, and where the individual layers of the sandwich are connected to each other, and where the nano-fibrous layer is created by an organic polymer material with areal weight of 0.05 to 0.3 g/m² and thickness from 90 to 150 nm, whereas the covering layer is selected from the group involving an unwoven spunbound fabric, an unwoven meltblown fabric, a fabric of cotton textile and/or a fabric mixture of cotton and polyester.

2. A barrier fabric according to claim 1, wherein the nano-fibrous layer is made from the hydrophilic polymer linear aliphatic polyamid of the polyamide group.

3. A barrier fabric according to claim 1, wherein the areal weight of nano-fibrous layer is within the range from 0.1 to 0.15 g/m² and the thickness is about 100 nm.

4. A barrier fabric according to claim 1, wherein the nano-fibrous layer comprises the additive of acaricides.

5. Barrier fabric with a nano-fibrous layer for mechanical capturing of organic substances which is formed by a composite structure that comprises a base material from unwoven spunbound fabric with areal weight of 15 to 50 g/m², at which is arranged at least one nano-fibrous layer, thus creating a barrier against the penetration of bacteria and viruses and other microorganisms through surgery gowns, mouth-screens, coverings or biological filters, where the nano-fibrous layer is formed of an organic hydrophobic polymer material made from polyurethane or from PVDF fluoro-polymer, or by their co-polymers, respectively, with areal weight of 0.05 to 0.2 g/m² and thickness ranging from 100 to 250 nm, and where the individual layers are connected to each other.

6. A barrier fabric according to claim 5, wherein the areal weight of the nano-fibrous layer is within the range from 0.1 to 0.15 g/m² and the thickness in the range of 150 to 170 nm.

7. A barrier fabric according to claim 5, wherein the nano-fibrous layer comprises an additive of a germicidal substance.

* * * * *